(12) United States Patent
Kittaka

(10) Patent No.: US 9,164,038 B2
(45) Date of Patent: Oct. 20, 2015

(54) FLUORESCENCE LIGHT DETECTION DEVICE AND FLUORESCENCE LIGHT DETECTION METHOD

(71) Applicant: Nippon Sheet Glass Company, Limited, Minato-ku, Tokyo (JP)

(72) Inventor: Shigeo Kittaka, Minato-ku (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 0 days.

(21) Appl. No.: 14/331,987

(22) Filed: Jul. 15, 2014

(65) Prior Publication Data

US 2015/0034840 A1 Feb. 5, 2015

(30) Foreign Application Priority Data

Aug. 1, 2013 (JP) .................................. 2013-160490

(51) Int. Cl.
*G01N 21/64* (2006.01)

(52) U.S. Cl.
CPC ...... *G01N 21/645* (2013.01); *G01N 2021/6463* (2013.01); *G01N 2021/6484* (2013.01)

(58) Field of Classification Search
CPC .................. G02B 21/0076; G02B 2021/6484; G02B 21/64; G02B 21/645; G02B 2021/6463
USPC ......................................................... 250/459.1
See application file for complete search history.

(56) References Cited

U.S. PATENT DOCUMENTS

| 5,112,127 | A | * | 5/1992 | Carrabba et al. ............... 356/301 |
| 5,657,404 | A | * | 8/1997 | Buchanan et al. ............... 385/12 |
| 2002/0007111 | A1 | * | 1/2002 | Deckert et al. ................. 600/177 |
| 2006/0017920 | A1 | * | 1/2006 | Tsuchiya et al. ............... 356/317 |
| 2013/0146754 | A1 | * | 6/2013 | Chang et al. ............. 250/227.23 |
| 2013/0209034 | A1 | * | 8/2013 | Jono et al. ......................... 385/33 |

FOREIGN PATENT DOCUMENTS

JP 2009-014379 A 1/2009

* cited by examiner

*Primary Examiner* — Marcus Taningco
(74) *Attorney, Agent, or Firm* — Sughrue Mion, PLLC

(57) ABSTRACT

A fluorescence light detection device includes an excitation light fiber having an excitation light emitting end configured to emit excitation light; a fluorescence light fiber having a fluorescence light incident end on which fluorescence light is incident; an objective lens arranged between where the excitation light emitting end and the fluorescence light incident end are located, and a sample; and a reflective member arranged between where the excitation light emitting end and the fluorescence light incident end are located, and the objective lens, and having two reflective surfaces facing in opposite directions. The two reflective surfaces of the reflective member are positioned between an optical axis of the excitation light fiber and an optical axis of the fluorescence light fiber.

16 Claims, 11 Drawing Sheets

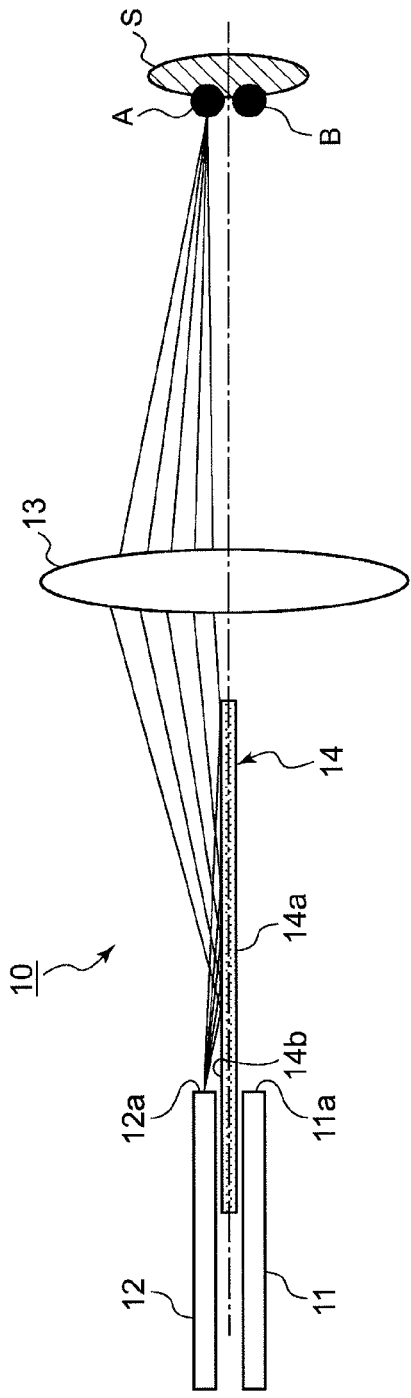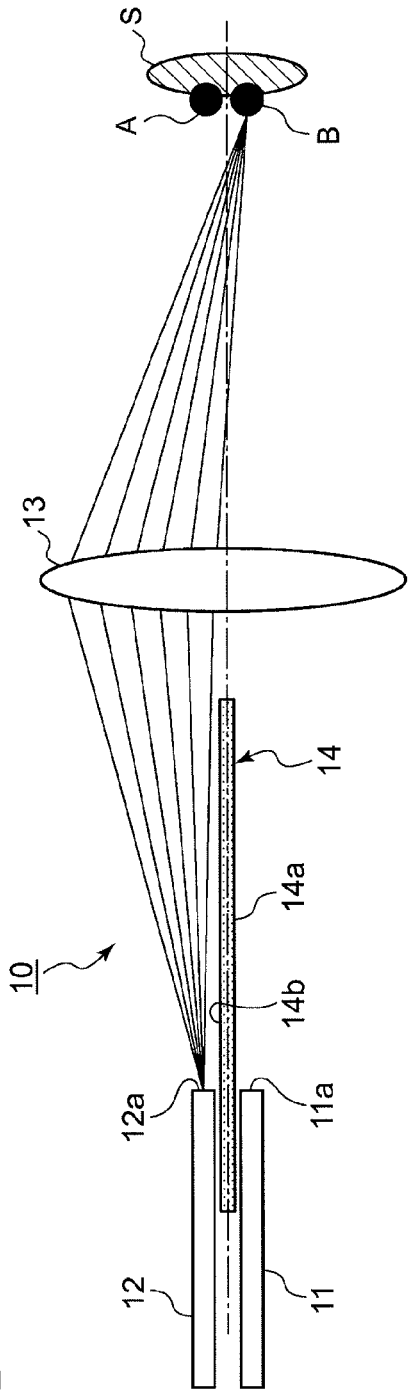

FLUORESCENCE LIGHT DETECTION DEVICE AND FLUORESCENCE LIGHT DETECTION METHOD

BACKGROUND OF THE INVENTION

1. Field of the Invention

The present invention relates to a fluorescence light detection device and a fluorescence light detection method configured to irradiate a test object with excitation light and detect fluorescence light produced by the test object.

2. Description of the Related Art

A growing number of fluorescence light detection devices have been used in the field of life science. A fluorescence light detection device is easy-to-use and has high detection sensitivity. A fluorescence light detection device may sometimes be used in combination with an amplification step for efficient quantitative detection of nucleic acid such as DNA marked by a fluorescent chemical substance.

For example, patent document 1 discloses a device including a light projection fiber for guiding excitation light onto a sample, a light receiving fiber for guiding fluorescence light produced by the sample, and a support means for supporting an emitting end of the light projection fiber and an incident end of the light receiving fiber.

[Patent document 1] JP2009-14379

However, a fluorescence light detection device in which a fiber for guiding excitation light and a fiber for guiding fluorescence light are provided as separate components as in patent document 1 has the following problem.

FIGS. 1A and 1B illustrate a problem with a fluorescence light detection device in which a fiber for guiding excitation light and a fiber for guiding fluorescence light are provided as separate components. FIG. 1A illustrates how excitation light emitted from an excitation light fiber 101 is focused by an objective lens 103 onto a sample S. FIG. 1B illustrates how fluorescence light emitted from a fluorescence light fiber 102 is focused by the objective lens 103 onto the sample S. In reality, the fluorescence light is produced in the sample S and travels toward the fluorescence light fiber 102 via the objective lens 103. For ease of understanding, the fluorescence light is considered as traveling in the opposite direction.

As shown in FIGS. 1A and 1B, given that the excitation light fiber 101 and the fluorescence light fiber 102 are provided as separate components, the image of the core end surface of the excitation light fiber 101 formed by the objective lens 103 on the sample S (hereinafter, referred to as "excitation light spot") does not coincide with the image of the core end surface of the fluorescence light fiber 102 formed by the objective lens 103 on the sample S (hereinafter, referred to as "fluorescence light spot"). The images are displaced from each other. For example, it is assumed that the excitation light spot is formed at point A and the fluorescence light spot is formed at point B in the configuration of FIGS. 1A and 1B. Since the intensity of excitation light is at maximum at the excitation light spot A, the intensity of fluorescence light produced by the sample S is also at maximum at the excitation light spot A. However, the fluorescence light produced at the excitation light spot A is not captured by the fluorescence light fiber 102. The principle of reversibility of light path tells that the light produced at the fluorescence light spot B is captured by the fluorescence light fiber 102 at the maximum solid angle. Since the fluorescence light spot B is not irradiated by the excitation light, however, fluorescence light is not produced at the fluorescence light spot B in the first place. In this case, the distance between the objective lens 103 and the sample S need be adjusted so as to capture fluorescence light in a portion outside the excitation light spot or the fluorescence light spot in which the beams overlap. For example, the sample S may be brought closer to the objective lens 103 from where it is in FIGS. 1A and 1B. In other words, a defocused state need be induced. Naturally, however, fluorescence light cannot be captured at a high efficiency in a defocused state.

Thus, given that the excitation light fiber 101 and the fluorescence light fiber 102 are provided as separate components, the excitation light spot A having rich potential of producing an intense fluorescent signal and the fluorescence light spot B from which the fluorescence light fiber 102 can capture produced fluorescence light most effectively do not coincide at all so that it is difficult to detect fluorescence light of high intensity. Patent document 1 does not explicitly teach an objective lens but similarly indicates existence of misalignment between a region irradiated by excitation light and a region from which fluorescence light can be captured.

SUMMARY OF THE INVENTION

In this background, a purpose of the present invention is to provide a fluorescence light detection device and a fluorescence light detection method in which the intensity of fluorescence light detected is improved.

To address the aforementioned purpose, a fluorescence light detection device according to one embodiment of the present invention is configured to irradiate a test object with excitation light and detect fluorescence light produced from the test object due to the excitation light, and comprises: an excitation light fiber having an excitation light emitting end configured to emit excitation light; a fluorescence light fiber having a fluorescence light incident end on which fluorescence light is incident; an objective lens arranged between where the excitation light emitting end and the fluorescence light incident end are located, and the test object; and a reflective member arranged between where the excitation light emitting end and the fluorescence light incident end are located, and the objective lens, and having two reflective surfaces facing in opposite directions. The two reflective surfaces of the reflective member are positioned between an optical axis of the excitation light fiber and an optical axis of the fluorescence light fiber.

The two reflective surfaces of the reflective member may be parallel to an optical axis of the excitation light fiber and an optical axis of the fluorescence light fiber.

The center between the two reflective surfaces may be located at the center between an optical axis of the excitation light fiber and an optical axis of the fluorescence light fiber.

The reflective member may be placed so that the two reflective surfaces extend from the excitation light emitting end and the fluorescence light incident end to a position in front of the objective lens.

The reflective member may extend beyond the excitation light emitting end and the fluorescence light incident end and into a space between the excitation light fiber and the fluorescence light fiber.

The reflective member may be a reflective plate configured to reflect light on both front and back surfaces.

The reflective member may be provided with two cuboid prisms placed such that flat surfaces thereof are spaced apart at a predetermined distance.

The fluorescence light detection device may further comprise an objective reflective member placed between the objective lens and the test object and having two reflective surfaces facing mutually opposite directions.

The objective lens may be configured as a single lens or a combination of a plurality of lenses.

The objective lens may be provided with two lenses and an interlens reflective member placed between the two lenses and having two reflective surfaces facing mutually opposite directions.

The fluorescence light detection device may further comprise a fluorescence light selection filter in front of the fluorescence light incident end. The fluorescence light detection device may further comprise an excitation light selection filter in front of the excitation light emitting end.

Another embodiment of the present invention also relates to a fluorescence light detection device configured to irradiate a test object with excitation light and detect fluorescence light produced from the test object due to the excitation light. The device comprises: one or a plurality of excitation light fibers having an excitation light emitting end; one or a plurality of fluorescence light fibers having a fluorescence light incident end on which fluorescence light is incident; an objective lens arranged between where the excitation light emitting end and the fluorescence light incident end are located, and the test object; and a reflective member arranged between where the excitation light emitting end and the fluorescence light incident end are located, and the objective lens, and having a total of 2n reflective surfaces, given that the total number of excitation light fibers and fluorescence light fibers is n. The excitation light fiber and the fluorescence light fiber are arranged such that optical axes are parallel to each other. Each of the excitation light fibers and the fluorescence light fibers is arranged at a vertex of a polygon with n sides when the fiber end surface is seen from the direction of optical axis of the fiber. The reflective plates are arranged such that the two reflective surfaces are positioned between adjacent fibers when the fiber end surface is seen from the direction of optical axis of the fiber.

Still another embodiment of the present invention relates to a method of detecting fluorescence light from a test object by using the aforementioned fluorescence light detection device.

The above method of detecting fluorescence light may comprise: adjusting a working distance of the objective lens such that a signal obtained based on the fluorescence light is maximized and/or variation in signals obtained based on the fluorescence light is minimized.

The above method of detecting fluorescence light may comprise: adjusting the angle formed by the optical axis of the excitation light fiber and/or the fluorescence light fiber and a surface of the test object such that a signal obtained based on the fluorescence light is maximized and/or variation in signals obtained based on the fluorescence light is minimized.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

FIGS. 4A and 4b illustrate rays emitted from the fluorescence light incident end of the fluorescence light fiber;

DETAILED DESCRIPTION OF THE INVENTION

The invention will now be described by reference to the preferred embodiments. This does not intend to limit the scope of the present invention, but to exemplify the invention.

A description will now be given of a fluorescence light detection device according to an embodiment of the present invention.

Figure 2:
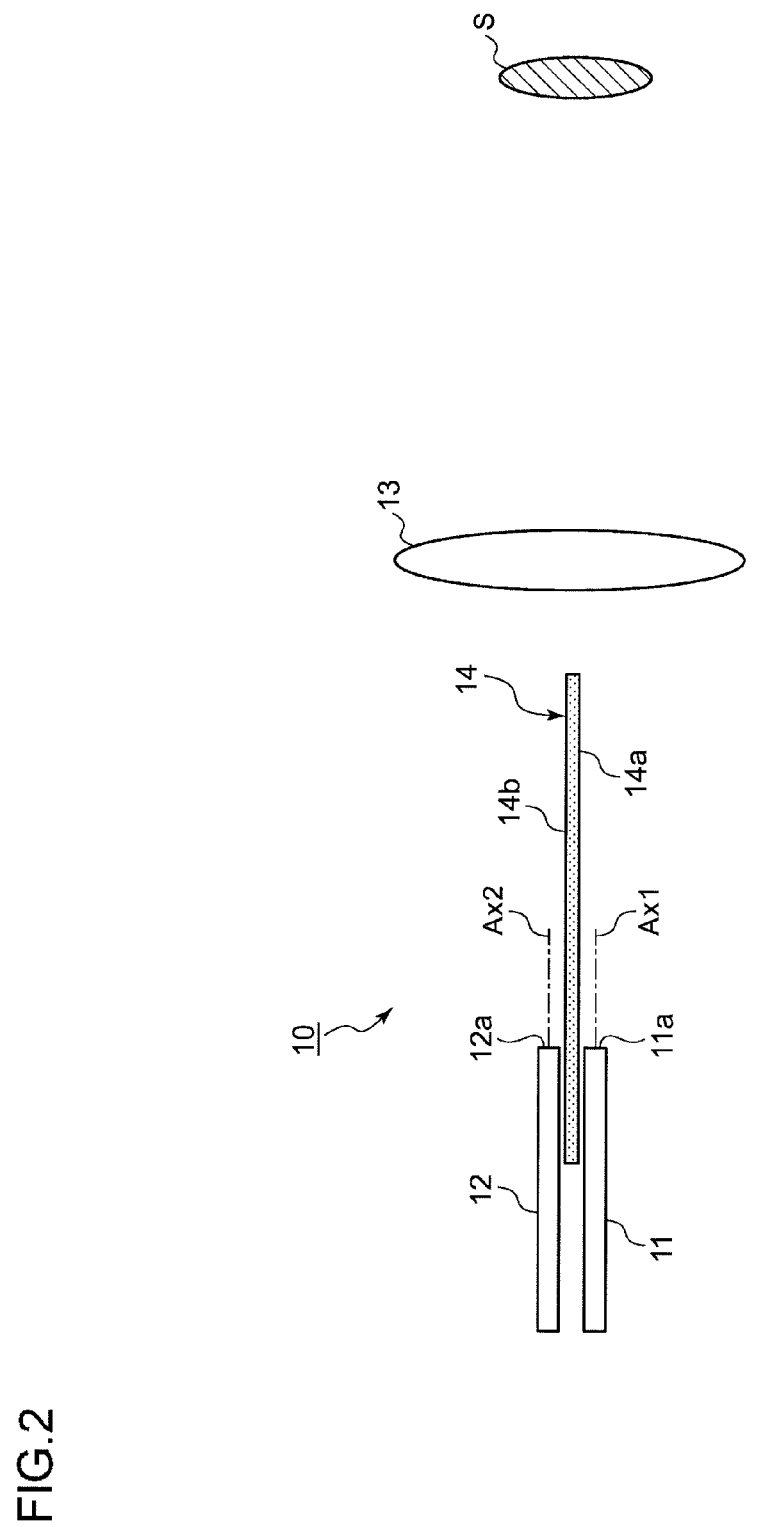
FIG. 2 illustrates a fluorescence light detection device according to an embodiment.

FIG. 2 illustrates a fluorescence light detection device 10 according to the embodiment. The fluorescence light detection device 10 is configured to irradiate a sample S (test object) with excitation light and detect the fluorescence light produced by the sample S.

As shown in FIG. 2, the fluorescence light detection device 10 is provided with an excitation light fiber 11 having an excitation light emitting end 11a for emitting an excitation light, a fluorescence light fiber 12 having a fluorescence light incident end 12a on which fluorescence light is incident, an objective lens 13 placed between the excitation light emitting end 11a/the fluorescence light incident end 12a and the sample S, and a reflective plate 14 placed between the excitation light emitting end 11a/the fluorescence light incident end 12a and the objective lens 13. As shown in FIG. 2, the excitation light fiber 11 and the fluorescence light fiber 12 are placed such that an optical axis Ax1 at the excitation light emitting end 11a and an optical axis Ax2 at the fluorescence light incident end 12a are parallel. The description here assumes that the objective lens 13 is an optical system that forms an inverted image, i.e., an optical system with a negative image magnification factor. However, the same advantage will be available if the objective lens 13 forms an erect image, i.e., an optical system with a positive image magnification factor. For the sake of convenience, FIG. 2 only shows one objective lens 13. However, for reasons of aberration and constraints on the working distance, the objective lens 13 may include a plurality of lenses or an optical element having focusing capabilities such as diffraction gratings.

Both the front and back surfaces of the reflective plate 14 are formed to be reflective (a first reflective surface 14a and a second reflective surface 14b). The first reflective surface 14a and the second reflective surface 14b are parallel to each other and face mutually opposite directions. The first reflective surface 14a and the second reflective surface 14b of the reflective plate 14 are located between the optical axis Ax1 at the excitation light emitting end 11a of the excitation light fiber 11 and the optical axis Ax2 at the fluorescence light incident end 12a of the fluorescence light fiber 12. The first reflective surface 14a of the reflective plate 14 is located toward the excitation light fiber 11 and the second reflective surface 14b is located toward the fluorescence light fiber 12. It is preferable that the first reflective surface 14a and the second reflective surface 14b be parallel to the optical axis Ax1 of the excitation light fiber 11 and the optical axis Ax2 of the fluorescence light fiber 12. It is further preferable that the center between the first reflective surface 14a and the second reflective surface 14b be located at the center between the optical axis Ax1 of the excitation light fiber 11 and the optical axis Ax2 of the fluorescence light fiber 12.

Figure 3A:
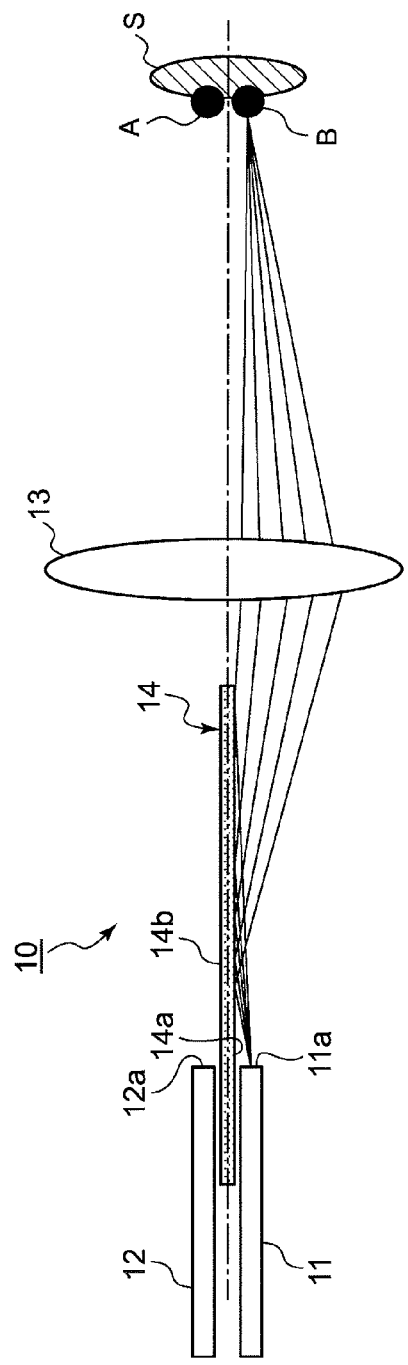
FIGS. 3A and 3B illustrate rays emitted from the excitation light emitting end of the excitation light fiber.
Figure 3B:
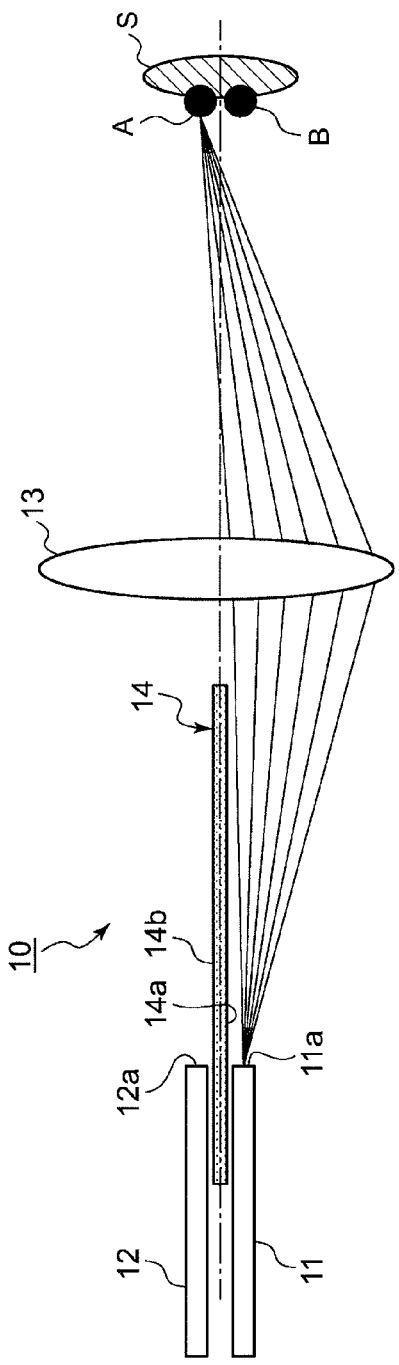

A description will now be given of the operation of the fluorescence light detection device 10 according to the embodiment with reference to FIGS. 3A-3B and FIGS. 4A-4B. FIGS. 3A and 3B illustrate rays emitted from the excitation light emitting end 11a of the excitation light fiber 11. FIGS. 4A and 4b illustrate rays emitted from the fluorescence light incident end 12a of the fluorescence light fiber 12. In FIGS. 4A and 4B, as in FIGS. 1A and 1B, the fluorescence light is conceived as traveling in the reverse direction for ease of understanding. In other words, the fluorescence light is conceived as being emitted from the fluorescence light fiber 12 so that a fluorescence light spot is formed by the objective lens 13 on the sample S.

As shown in FIG. 3A, about half of the excitation light from the excitation light fiber 11 of the fluorescence light detection device 10 according to the embodiment is reflected by the first reflective surface 14a of the reflective plate 14 before being focused by the objective lens 13 to form an excitation light spot at point B on the sample S. Concurrently, as shown in FIG. 3B, about half of the excitation light not reaching the first reflective surface 14a of the reflective plate 14 is focused by the objective lens 13 to form an excitation light spot at point A on the sample S. As a result, excitation light spots of substantially the same brightness can be formed at points A and B.

Meanwhile, as shown in FIG. 4A, about half of the fluorescence light from the fluorescence light fiber 12 is reflected by the second reflective surface 14b of the reflective plate 14 before being focused by the objective lens 13 to form a fluorescence light spot at point A on the sample S. Concurrently, about half of the fluorescence light not reaching the second reflective surface 14b of the reflective plate 14 is focused by the objective lens 13 to form a fluorescence light spot at point B on the sample S. As a result, fluorescence light spots of substantially the same brightness can be formed at points A and B.

Thus, in the fluorescence light detection device 10 according to the embodiment, the excitation light spot and the fluorescence light spot coincide at two points, namely points A and B. In the neighborhood of the these spots, the intensity of excitation light irradiating the sample S is at maximum so that the intensity of fluorescence light produced by the sample S is also at maximum. The principle of reversibility of light path tells that fluorescence light produced in the neighborhood of the spots is captured by the fluorescence light fiber 12 at a large solid angle.

In other words, the excitation light emitted from the excitation light emitting end 11a of the excitation light fiber 11 and reflected by the first reflective surface 14a of the reflective plate 14 forms an excitation light spot at point B on the sample via the objective lens 13, as shown in FIG. 3A. As can be seen in FIG. 4B, the fluorescence light produced by the excitation light spot at point B on the sample S is incident on the fluorescence light incident end 12a of the fluorescence light fiber 12 via the objective lens 13 without being reflected by the second reflective surface 14b.

Meanwhile, the excitation light emitted from the excitation light emitting end 11a of the excitation light fiber 11 and not reaching the first reflective surface 14a of the reflective plate 14 forms an excitation light spot at point A on the sample S via the objective lens 13. As can be seen in FIG. 4A, the fluorescence light produced by the excitation light spot at point A on the sample S is incident on the fluorescence light incident end 12a of the fluorescence light fiber 12 via the objective lens 13, reflected by the second reflective surface 14b.

Thus, according to the fluorescence light detection device 10 of the embodiment, the excitation light spot and the fluorescence light spot are ensured to coincide so that the intensity of fluorescence light detected is improved. Strictly speaking, point A at which the excitation light converges in FIG. 3B and point A at which the fluorescence light converges in FIG. 4A do not completely coincide and are displaced from each other by a length defined by multiplying the thickness of the reflective plate 14 by the image magnification factor of the objective lens 13. However, the impact from displacement is negligible if the thickness of the reflective plate 14 is sufficiently smaller than the core diameter of the excitation light fiber 11 and the fluorescence light fiber 12.

In describing the embodiment, it is assumed that the objective lens 13 is an optical system that forms an inverted image. In other words, referring to FIGS. 3A and 3B, the excitation light emitted from the excitation light emitting end 11a forms a path connecting (a) the excitation light emitting end 11a→the first reflective surface 14a→the objective lens 13→point B on the sample S, and a path connecting (b) the excitation light emitting end 11a→the objective lens 13→point A on the sample S. Referring to FIGS. 4A and 4B, the fluorescence light emitted from point A or point B on the sample S forms a path connecting (a) point A on the sample S→the objective lens 13→the second reflective surface 14b→the fluorescence light incident end 12a, or a path connecting (b) point B on the sample S→the objective lens 13→the fluorescence light incident end 12a.

Meanwhile, if the objective lens 13 is an optical system that forms an erect image (not shown), the excitation light emitted from the excitation light emitting end 11a can form a path connecting (a') the excitation light emitting end 11a→the first reflective surface 14a→the objective lens 13→point A on the sample S, and a path connecting (b') the excitation light emitting end 11a→the objective lens 13→point B on the sample S. It would be understood that the fluorescence light emitted from point A or point B on the sample S can form a path connecting (a') point A on the sample S→the objective lens 13→the fluorescence light incident end 12a, or a path connecting (b') point B on the sample S→the objective lens 13→the second reflective surface 14b→the fluorescence light incident end 12a. It is within the design capabilities of a skilled person to determine whether to use an erecting or inverting optical system. In either case, the benefit of the reflective plate placed between the light emitting end or the light incident end and the objective lens can be obtained.

Figure 1A:
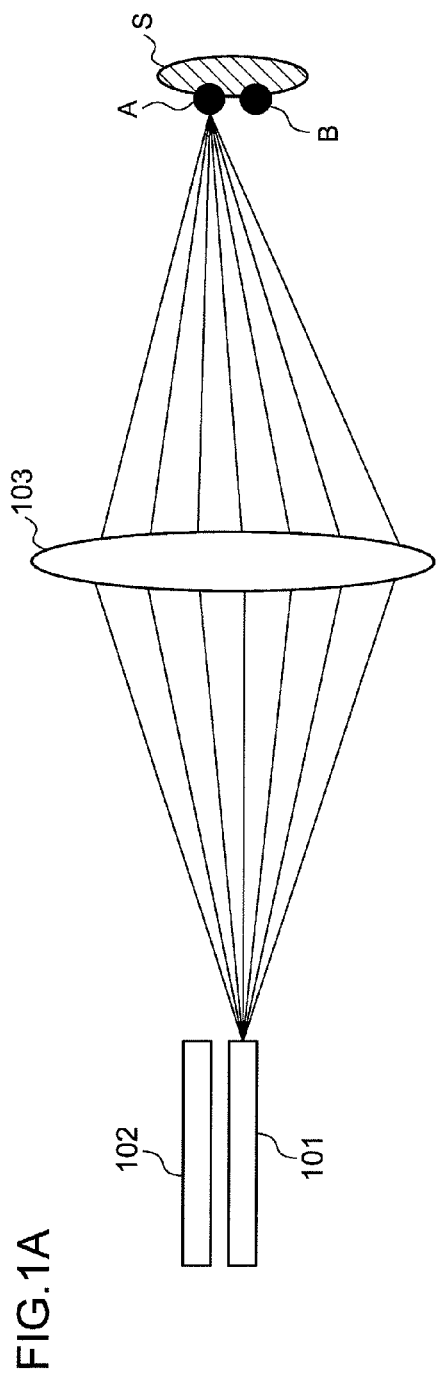
FIGS. 1A and 1B illustrate a problem with a fluorescence light detection device in which a fiber for guiding excitation light and a fiber for guiding fluorescence light are provided as separate components.
Figure 1B:
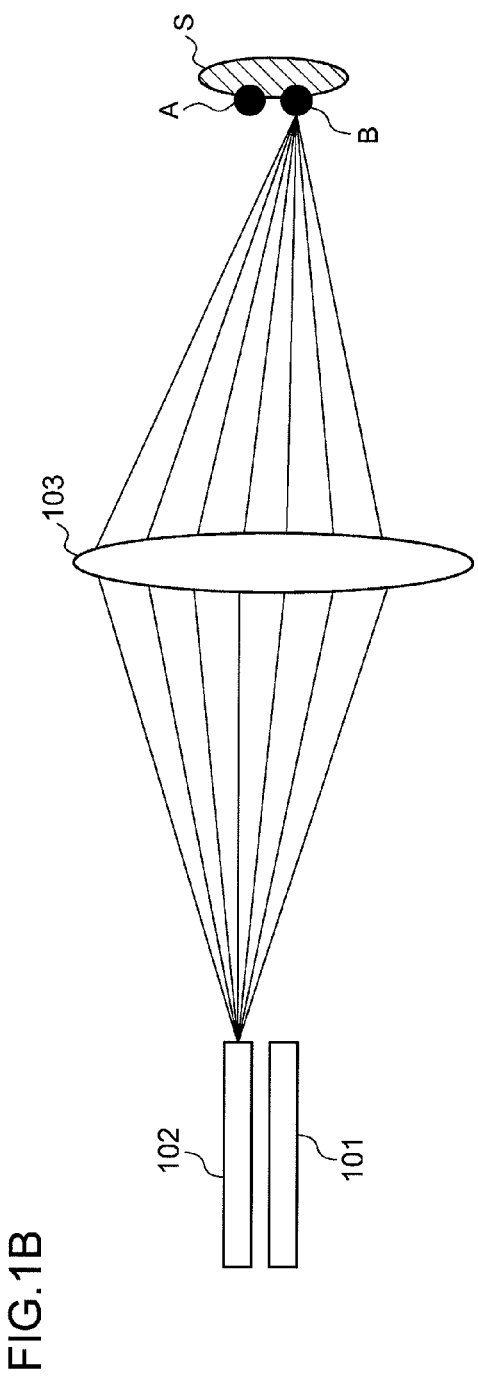

The fluorescence light detection device 10 has the following advantages. As shown in FIGS. 1A and 1B, the major portion of the objective lens 103 of the fluorescence light detection device not provided with a reflective plate permits passage of rays of excitation light and also permits passage of rays of fluorescence light. For this reason, the reflected light, scattering light, and fluorescence light produced by the excitation light from the objective lens 103 will be optical noise entering the fluorescence light fiber 102, resulting in reduction in precision of measuring fluorescence light.

Meanwhile, in the fluorescence light detection device 10 according to the embodiment, the area in which the excitation light passes and the area in which the fluorescence light passes are substantially isolated by providing the reflective plate 14 between the excitation light emitting end 11a/the fluorescence light incident end 12a and the objective lens 13. In other words, the excitation light from the excitation light fiber 11 mainly passes through the lower half of the objective lens 13 as shown in FIGS. 3A and 3B, but only the rays of the fluorescence light produced on sample S that mainly pass through the upper half of the objective lens 13 are incident on the fluorescence light fiber 12 so that the area in which the excitation light and the fluorescence light overlap can be reduced. By forming the reflective plate 14 of non-transparent material, cross talk via the reflective plate 14 does not occur. Accordingly, faint reflected light, scattering light, and fluorescence light produced in the objective lens 13 directly irradiated by the excitation light can hardly be captured by the fluorescence light fiber 12 so that optical noise is reduced and the precision of measuring fluorescence light is improved.

When using the fluorescence light detection device 10 according to the embodiment, the working distance of the objective lens 13 may be adjusted such that the signal obtained based on the fluorescence light is maximized and/or variation in signals obtained based on the fluorescence light is minimized. The angle formed by the optical axes of the excitation light fiber 11 and/or the fluorescence light fiber 12 and the surface of the sample S may be adjusted such that the signal obtained based on the fluorescence light is maximized and/or variation in signals obtained based on the fluorescence light is minimized. An exemplary embodiment in which the angle is adjusted as such is described below as the second exemplary embodiment.

Figure 5:
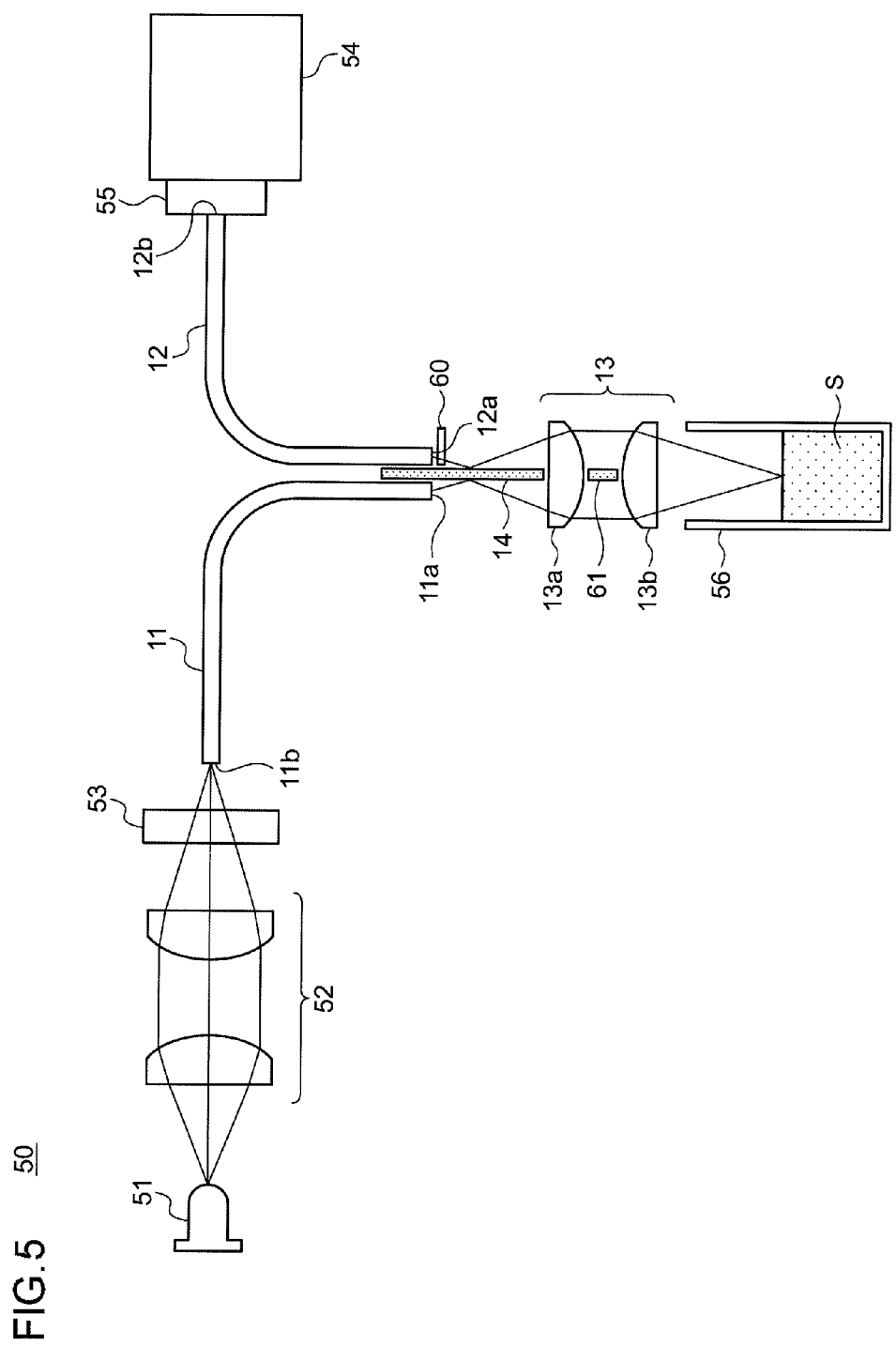
FIG. 5 illustrates a fluorescence light detection device according to the first exemplary embodiment of the present invention.

A description will be given of exemplary embodiments of the present invention. FIG. 5 illustrates a fluorescence light detection device 50 according to the first exemplary embodiment. As shown in FIG. 5, the fluorescence light detection device 50 includes an excitation light source 51, an excitation light fiber 11, a fluorescence light fiber 12, a focusing lens 52, an excitation light filter 53, an objective lens 13, a reflective plate 14, a photomultiplier tube 54 as a fluorescence light detector, a fluorescence light filter 55, and a fluorescence light filter 60.

A bullet type green LED (NSPG300D from NICHIA CORPORATION (central wavelength (catalog value)=about 525 nm)) is used as the excitation light source 51 and is driven by a current with a peak value of 40 mA and a frequency of 110 Hz to emit pulses of light. The focusing lens 52 is embodied by two plano-convex lenses (diameter=12 mm, focal length=18 mm) made of synthetic quartz. The light beams from the excitation light source 51 are turned into substantially parallel light beams by first plano-convex lens and the substantially parallel light beams are focused by second plano-convex lens. An incident end 11b of the excitation light fiber 11 is placed in the neighborhood of the focal point. UV600-660-710P28 from a U.S. company CeramOpticIndustries, Inc. (core diameter=0.6 mm, numerical aperture NA=0.3) is used as the excitation light fiber 11. Between the focusing lens 52 and the incident end 11b of the excitation light fiber 11 is placed a fluorescence light bandpass filter from Edmund Optics Japan (passband central wavelength=534.5 nm, full width at half maximum=48 nm) to embody the excitation light filter 53, so as to remove light of undesired wavelengths from the excitation light.

The excitation light propagating through the excitation light fiber 11 and emitted from the excitation light emitting end 11a is focused by the objective lens 13 on the sample S (i.e., water solution containing a fluorescent substance). The fluorescence light produced in the sample S is focused by the objective lens 13 on the fluorescence light incident end 12a of the fluorescence light fiber 12. The sample S is accommodated in a cylindrical cell 56 made of black resin having an inner diameter of 6.5 mm and a depth of 11 mm.

The same type of fiber as used for the excitation light fiber 11 is used as the fluorescence light fiber 12. The amount of energy of the fluorescence light propagating through the fluorescence light fiber 12 is measured by the PMT 54. H9306-04 from Hamamatsu Photonics K.K is used as the PMT 54. Between the emitting end 12b of the fluorescence light fiber 12 and the PMT 54 are placed, one each, a predetermined bandpass filter (passband wavelength range 600-640 nm) and a fluorescence light bandpass filter from Edmund Optics Japan (passband central wavelength=624 nm, full width at half maximum=46 nm) to embody the fluorescence light filter 55, so as to remove light of wavelength other than that of the fluorescence light produced in the sample S. Of the signals received by the PMT 54, those components having the same frequency (110 Hz) as the pulses of light from the excitation light source 51 are selectively detected and used to yield output values.

Figure 6:
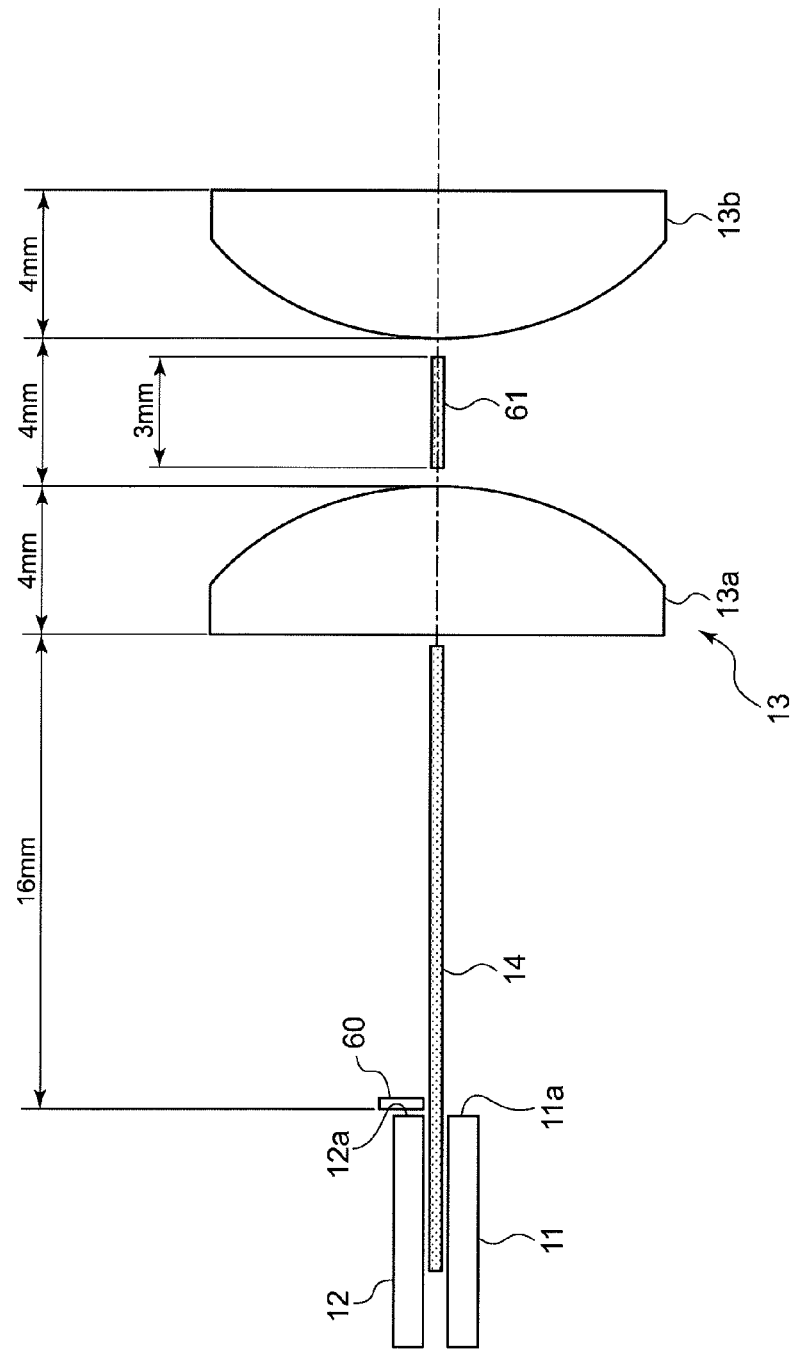
FIG. 6 is an enlarged view of the neighborhood of the objective lens in the fluorescence light detection device shown in FIG. 5.

FIG. 6 is an enlarged view of the neighborhood of the objective lens 13 in the fluorescence light detection device shown in FIG. 5. The interval between the optical axes at the excitation light emitting end 11a of the excitation light fiber 11 and the fluorescence light incident end 12a of the fluorescence light fiber 12 is 0.8 mm. The shim tape SFGSM0.05 from MISUMI Corporation (stainless plate with a thickness of 0.05 mm) is used as the reflective plate 14. The width of the reflective plate 14 (length in the direction perpendicular to the plane of paper of FIG. 6) is 12 mm.

In the first exemplary embodiment, the reflective plate 14 is placed so that the two reflective surfaces extend from the excitation light emitting end 11a and the fluorescence light incident end 12a to a position immediately in front of incident surface of the objective lens 13. This can enhance the advantage of increasing the intensity of fluorescence light detected and improving the precision of measuring fluorescence light. In further accordance with the first exemplary embodiment, the reflective plate 14 extends beyond the excitation light emitting end 11a and the fluorescence light incident end 12a and into a space between the excitation light fiber 11 and the fluorescence light fiber 12. This can further enhance the advantage of increasing the intensity of fluorescence light detected and improving the precision of measuring fluorescence light.

In the first exemplary embodiment, the objective lens 13 is embodied by two (13a, 13b) plano-convex lenses (diameter=9 mm, focal length=12 mm) made of synthetic quartz arranged such that the convex surfaces face each other. A reflective plate having two reflective surfaces facing mutually opposite directions (referred to as "interlens reflective plate") 61 is placed between the two plano-convex lenses 13a and 13b. Like the reflective plate 14, the interlens reflective plate 61 helps increase intensity of fluorescence light detected and improve the precision of measuring fluorescence light.

In further accordance with the first exemplary embodiment, a fluorescence light filter 60 for selectively transmitting fluorescence light is placed in front of the fluorescence light incident end 12a of the fluorescence light fiber 12. The fluorescence light filter 60 is a bandpass filter having a passband wavelength range 600 nm-640 nm. Further, an excitation light selection filter (not shown) for selectively transmitting excitation light may be placed in front of the excitation light emitting end 11a of the excitation light fiber 11.

The output values of the PMT 54 were measured in a dark room under the following four conditions, using the fluorescence light detection device 50 according to the first exemplary embodiment illustrated in FIGS. 5 and 6. More specifically, about 300 measurements were performed in a period of 30 seconds for measurement and an average and dispersion (standard deviation) of the output values were calculated.

A 300 mm$^3$ Resorufin water solution with a density 10 nM (10 nanomoles per liter) was contained in a cell as a sample. The position of the cell was adjusted so that the output of the PMT 54 is maximized. The following results were obtained.

(1) The average output of 676.6 mV of the PMT 54 and the standard deviation of 1.393 mV were obtained from the Resorufin water solution.

(2) A blank test was conducted by taking measurements from ultrapure water for use in liquid chromatograph/mass analysis from Wako Pure Chemical Industries, Ltd. contained in a cell 56. The average output of 33.6 mV of the PMT 54 and the standard deviation of 0.303 mV were obtained.

(3) When the sample S and the cell 56 were removed, the average output of the PMT 54 was 3.9 mV and the standard deviation was 0.069 mV.

(4) In a condition in which no light enters the light receiving part of the PMT 54, the average output of 2.5 mV and the standard deviation of 0.042 mV were obtained. These data represent electrical noise in the PMT 54 and the detection circuit.

Based on the above result, the output difference between (1) and (2), i.e., 643 mV is determined to be the measurement of the amount of fluorescence from the Resorufin water solution. The output difference 29.7 mV between (2) and (3) represents optical noise originating from scattering, reflection, and fluorescence light due to the solvent (ultrapure water) and the cell 56. The output difference 1.4 mV between (3) and (4) represents optical noise originating from scattering, reflection, and fluorescence light in the objective lens 13. Given that the amount of fluorescence light from the Resorufin water solution is proportional to the density of Resorufin in the sample, the standard deviation in the blank test represents noise, and the value three times the noise represents the measurable limit density, the measurable limit density is determined to be 14 pM (picomoles per liter) based on the following expression. The measurable limit density is defined as the smallest value that can indicate detection of a target chemical substance with high reliability.

$$10 \text{ nM} \times (3 \times 0.303/643) = 0.014 \text{ nM} = 14 \text{ pM}$$

A description will now be given of a comparative example to verify the result of measurement in the first exemplary embodiment. The reflective plate 14 and the interlens reflective plate 61 are removed from the fluorescence light detection device 50 shown in FIGS. 5 and 6 and a measurement similar to that of the first exemplary embodiment was performed. The result of measurement is shown below.

(1') The average output of 306.5 mV of the PMT 54 and the standard deviation of 1.029 mV were obtained from the Resorufin water solution.

(2') In a blank test, the average output of 24.3 mV of the PMT 54 and the standard deviation of 0.264 mV were obtained.

(3') When the sample S and the cell 56 were removed, the average output of the PMT 54 was 14.4 mV and the standard deviation was 0.181 mV.

(4') In a condition in which no light enters the light receiving part of the PMT 54, the average output of 2.5 mV and the standard deviation of 0.042 mV were obtained.

Based on the above result, the output difference between (1') and (2'), i.e., 282.2 mV is determined to be the measurement of the amount of fluorescence from the Resorufin water solution. The output difference 9.9 mV between (2') and (3') represents optical noise originating from scattering, reflection, and fluorescence light due to the solvent (ultrapure water) and the cell 56. The output difference 11.9 mV between (3') and (4') represents optical noise originating from scattering, reflection, and fluorescence light in the objective lens 13. The measurable limit density is determined to be 28 pM based on the following expression.

$$10 \text{ nM} \times (3 \times 0.264/282.2) = 0.028 \text{ nM} = 28 \text{ pM}$$

A summary of the first exemplary embodiment and the comparative example is given below.

(A) Intensity of Fluorescence Light Detected from Resorufin Water Solution

The intensity of fluorescence light about 2.3 times that of the comparative embodiment is detected in the first exemplary embodiment (643 mV/282.2 mV=2.28).

(B) Measurable Limit Density

The first exemplary embodiment provides capability to detect fluorescence light from the Resorufin water solution with a density about ½ that of the comparative example (14 pM/28 pM=½).

(C) Optical Noise Originating from the Objective Lens

According to the first exemplary embodiment, noise originating from the objective lens 13 is reduced to a level about 1/10 that of the comparative example (1.4 mV/11.9 mV=0.12).

Figure 7:
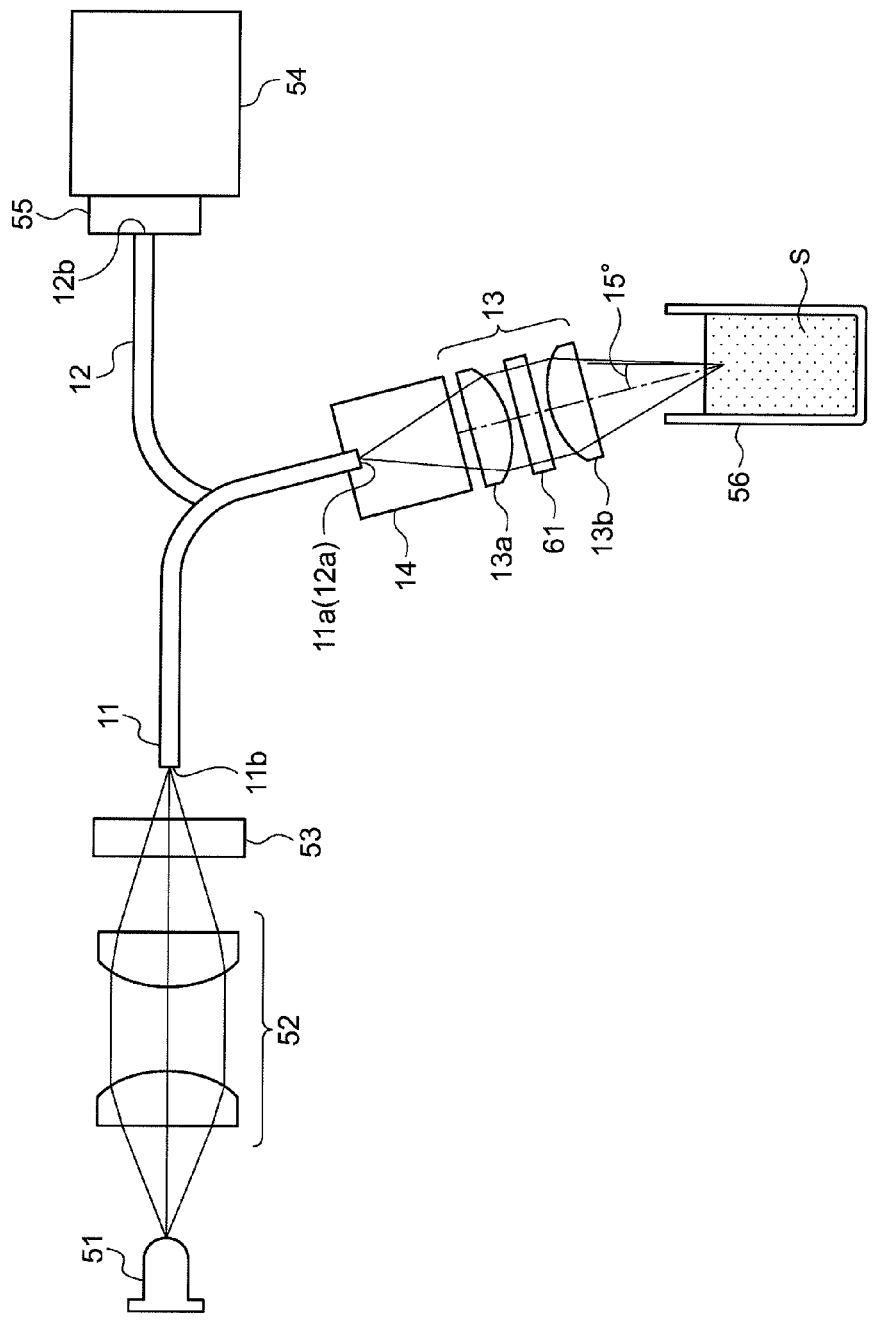
FIG. 7 illustrates a fluorescence light detection device according to the second exemplary embodiment of the present invention.

FIG. 7 illustrates a fluorescence light detection device 62 according to the second exemplary embodiment of the present invention. As shown in FIG. 7, the optical axis of the objective lens 13 according to the embodiment is inclined 15° from an axis perpendicular to the surface of the sample S so that the excitation light is diagonally incident on the surface of the sample S. The arrangement is designed to reduce optical noise produced as a result of the excitation light reflected by the surface of the sample S entering the fluorescence light fiber 12. In the arrangement of FIG. 7, the excitation light emitting end 11a of the excitation light fiber 11 and the fluorescence light incident end 12a of the fluorescence light fiber 12 are arranged in the direction perpendicular to the plane of paper.

In the second exemplary embodiment, a set of three filters, including a predetermined bandpass filter (passband wavelength range 600-640 nm), a fluorescence light bandpass filter from Edmund Optics Japan (passband central wavelength-624 nm, full width at half maximum-46 nm), and a longpass filter OG590 from Edmund Optics Japan, is used as the fluorescence light filter 55 between the emitting end 12b of the fluorescence light fiber 12 and the PMT 54. The specification of the other constituting elements is identical to that of the first exemplary embodiment shown in FIGS. 5 and 6.

The output values of the PMT 54 were measured in a dark room under the following four conditions, using the fluorescence light detection device 62 illustrated in FIG. 7. More specifically, about 300 measurements were performed in a period of 30 seconds for measurement and an average and dispersion (standard deviation) of the output values were calculated.

As a sample, a 300 mm$^3$ Resorufin water solution with a density 10 nM (10 nanomoles per liter) was contained in a cell. The position of the cell was adjusted so that the output of the PMT 54 is maximized. The following results were obtained.

(1) The average output of 545.9 mV of the PMT 54 and the standard deviation of 1.273 mV were obtained from the Resorufin water solution.

(2) A blank test was conducted by taking measurements from ultrapure water for use in liquid chromatograph/mass analysis from Wako Pure Chemical Industries, Ltd. contained in a cell. The average output of 15.7 mV of the PMT 54 and the standard deviation of 0.196 mV were obtained.

(3) When the sample S and the cell 56 were removed, the average output of the PMT 54 was 3.9 mV and the standard deviation was 0.075 mV.

(4) In a condition in which no light enters the light receiving part of the PMT 54, the average output of 2.5 mV and the standard deviation of 0.042 mV were obtained. These data represent electrical noise in the PMT 54 and the detection circuit.

Based on the above result, the output difference between (1) and (2), i.e., 530.2 mV is determined to be the measurement of the amount of fluorescence from the Resorufin water solution. The output difference 11.8 mV between (2) and (3) represents optical noise originating from scattering, reflection, and fluorescence light due to the solvent (ultrapure water) and the cell 56. The output difference 1.4 mV between (3) and (4) represents optical noise originating from scattering, reflection, and fluorescence light in the objective lens 13. Given that the amount of fluorescence light from the Resorufin water solution is proportional to the density of Resorufin in the sample, the standard deviation in the blank context represents noise, and the value three times the noise represents the measurable limit density, the measurable limit density is determined to be 11 pM (picomoles per liter) based on the following expression. The measurable limit density is defined as the smallest value that can indicate detection of a target chemical substance with high reliability.

$$10 \text{ nM} \times (3 \times 0.196/530.2) = 0.011 \text{ nM} = 11 \text{ pM}$$

A description will now be given of a comparative example to verify the result of measurement in the second exemplary embodiment. The reflective plate 14 and the interlens reflective plate 61 are removed from the fluorescence light detection device 62 shown in FIG. 7 and a measurement similar to that of the second exemplary embodiment was performed. The result of measurement is shown below.

(1') The average output of 300.8 mV of the PMT 54 and the standard deviation of 0.937 mV were obtained from the Resorufin water solution.

(2') In a blank test, the average output of 24.4 mV of the PMT 54 and the standard deviation of 0.274 mV were obtained.

(3') When the sample S and the cell 56 were removed, the average output of the PMT 54 was 14.4 mV and the standard deviation was 0.193 mV.

(4') In a condition in which no light enters the light receiving part of the PMT 54, the average output of 2.5 mV and the standard deviation of 0.042 mV were obtained.

Based on the above result, the output difference between (1') and (2'), i.e., 276.4 mV is determined to be the measurement of the amount of fluorescence from the Resorufin water solution. The output difference 10 mV between (2') and (3') represents optical noise originating from scattering, reflection, and fluorescence light due to the solvent (ultrapure water) and the cell. The output difference 11.9 mV between (3') and (4') represents optical noise originating from scattering, reflection, and fluorescence light in the objective lens 13. The measurable limit density is determined to be 30 pM based on the following expression.

$$10 \text{ nM} \times (3 \times 0.274/276.4) = 0.030 \text{ nM} = 30 \text{ pM}$$

A summary of the second exemplary embodiment and the comparative example is given below.

A) Intensity of Fluorescence Light Detected from Resorufin Water Solution

The intensity of fluorescence light about twice that of the comparative embodiment is detected in the second exemplary embodiment (530.2 mV/276.4 mV=1.92).

(B) Measurable Limit Density

The second exemplary embodiment provides capability to detect fluorescence light from the Resorufin water solution with a density about ⅓ that of the comparative example (11 pM/30 pM=0.37).

(C) Optical Noise Originating from the Objective Lens

According to the second exemplary embodiment, noise originating from the objective lens 13 is reduced to a level about 1/10 that of the comparative example (1.4 mV/11.9 mV=0.12).

Figure 8:
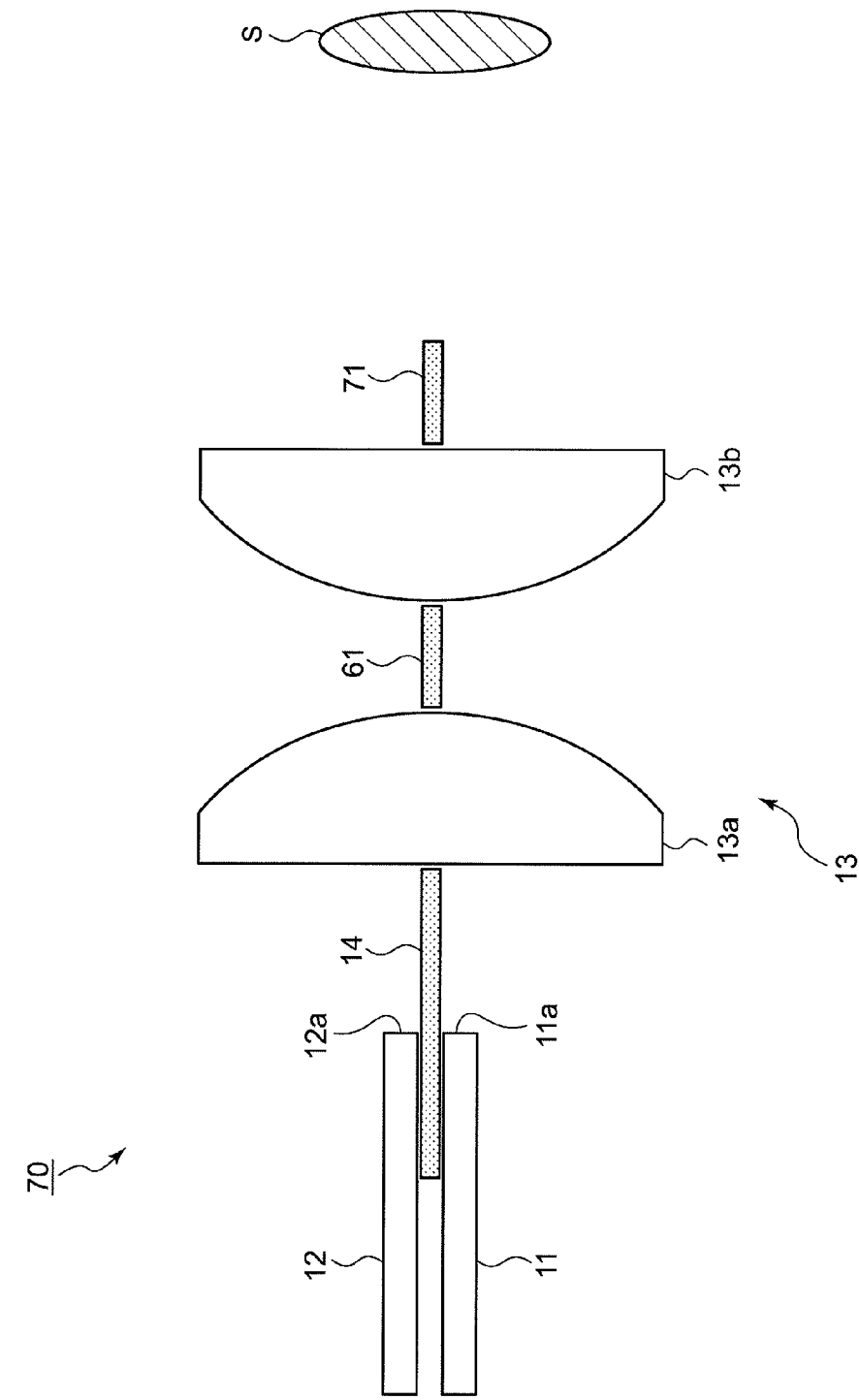
FIG. 8 illustrates a fluorescence light detection device according to another embodiment of the present invention.

FIG. 8 illustrates a fluorescence light detection device 70 according to another embodiment of the present invention. In addition to the reflective plate 14 and the interlens reflective plate 61, the fluorescence light detection device 70 according to this embodiment is further provided with a reflective plate 71 (referred to as "objective reflective plate") 71 placed between the objective lens 13 and the sample S. Like the reflective plate 14 and the interlens reflective plate 61, the objective reflective plate 71 is provided with two reflective surfaces facing mutually opposite directions and extends from the emitting surface of the objective lens 13 toward the sample S. By providing the objective reflective plate 71 as in this embodiment, the area in which the excitation light passes and the area in which the fluorescence light passes are more properly isolated so that optical noise is further reduced and the precision of measuring fluorescence light is further improved.

Figure 9:
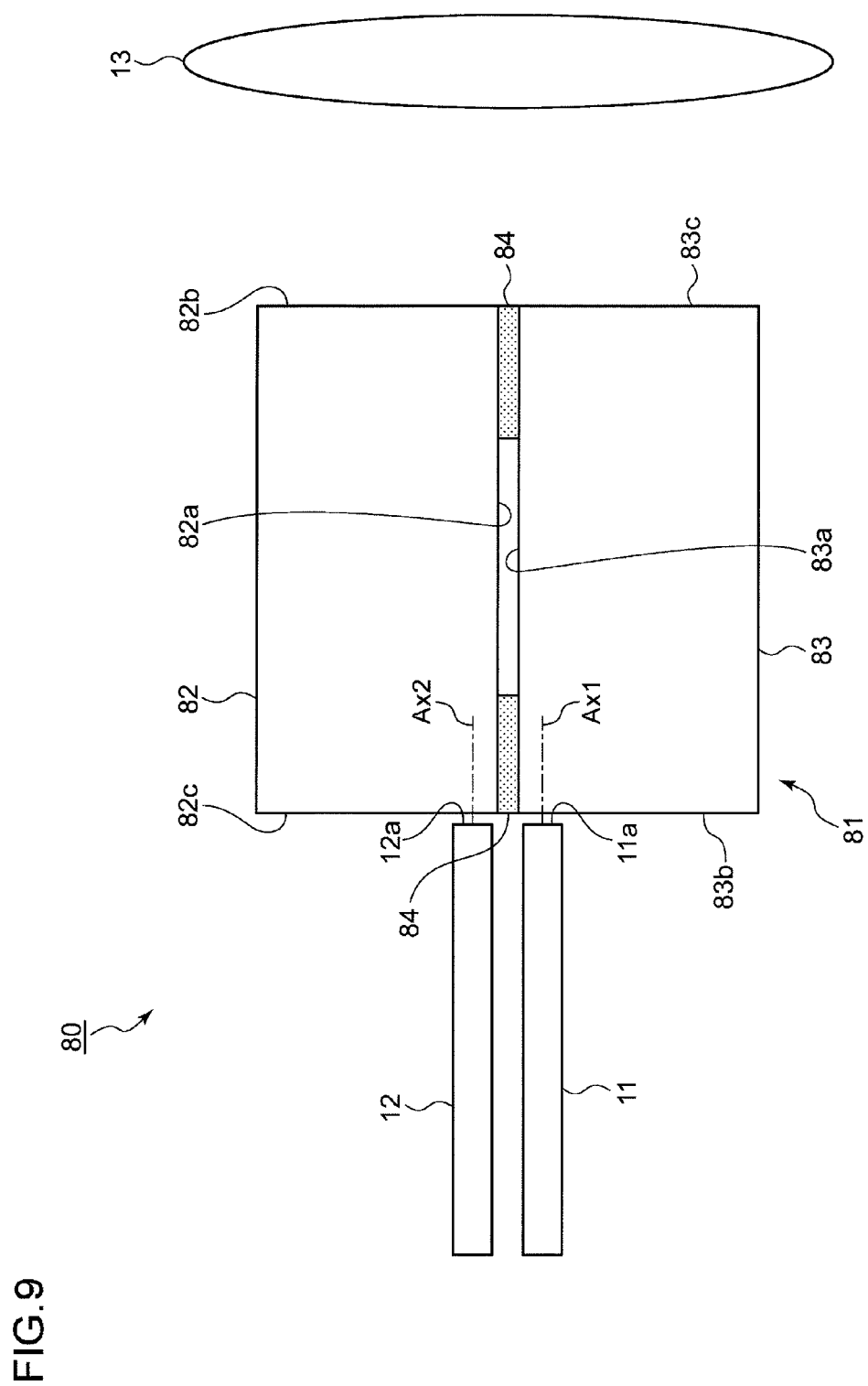
FIG. 9 illustrates a fluorescence light detection device according to still another alternative embodiment of the present invention.

FIG. 9 illustrates a fluorescence light detection device 80 according to still another alternative embodiment of the present invention. In the fluorescence light detection device 80 according to this embodiment, a reflective member 81 is provided between the excitation light emitting end 11a/the fluorescence light incident end 12a and the objective lens 13 in place of the reflective plate. The reflective member 81 is provided with two cuboid prisms 82 and 83. The two cuboid prisms are placed such that flat surfaces 82a and 83a are spaced apart at a predetermined distance via a spacer 84. By placing the two cuboid prisms 82 and 83 so as to sandwich an air layer in between, the flat surfaces 82a and 83a function as two total reflection surfaces. The two total reflection surfaces are parallel to each other and face mutually opposite directions.

The two total reflection surfaces 82a and 83a of the reflective member 81 are located between the optical axis Ax1 of the excitation light fiber 11 and the optical axis Ax2 of the fluorescence light fiber 12. It is preferable that the two total reflection surfaces 82a and 83a be parallel to the optical axis Ax1 of the excitation light fiber 11 and the optical axis Ax2 of the fluorescence light fiber 12. It is further preferable that the center between the two total reflection surfaces 82a and 83a is located at the center between the optical axis Ax1 of the excitation light fiber 11 and the optical axis Ax2 of the fluorescence light fiber 12.

In the fluorescence light detection device 80 according to the embodiment, the excitation light from the excitation light fiber 11 is incident on the cuboid prism 83 via an end surface 83b of the cuboid prism 83 facing the excitation light fiber 11. About half of the excitation light incident on the cuboid prism 83 is reflected by the total reflection surface 83a before being emitted from an end surface 83c facing away from the excitation light fiber 11 and forms an excitation light spot on a point of the sample via the objective lens 13. Concurrently, about half of the excitation light incident on the cuboid prism 83 and not reaching the total reflection surface 83a is emitted from the end surface 83c and forms an excitation light spot on another spot on the sample via the objective lens 13.

The fluorescence light produced at the two excitation light spots on the sample is transmitted through the objective lens 13 and is incident on the cuboid prism 82 via an end surface 82b of the cuboid prism 82 facing away from the fluorescence light fiber 12. About half of the fluorescence light incident on the cuboid prism 82 is reflected by the total reflection surface 82a before being emitted from an end surface 82c facing the fluorescence light fiber 12 and captured by the fluorescence light fiber 12 via the fluorescence light incident end 12a. Concurrently, about half of the fluorescence light incident on the cuboid prism 82 and not reaching the total reflection surface 82a is emitted from the end surface 82c and captured by the fluorescence light fiber 12 via the fluorescence light incident end 12a.

Like the fluorescence light detection device 10 described with reference to FIGS. 2-4, the fluorescence light detection device 80 according to this embodiment is also capable of increasing the intensity of fluorescence light detected and improving the precision of measuring fluorescence light.

Figure 10A:
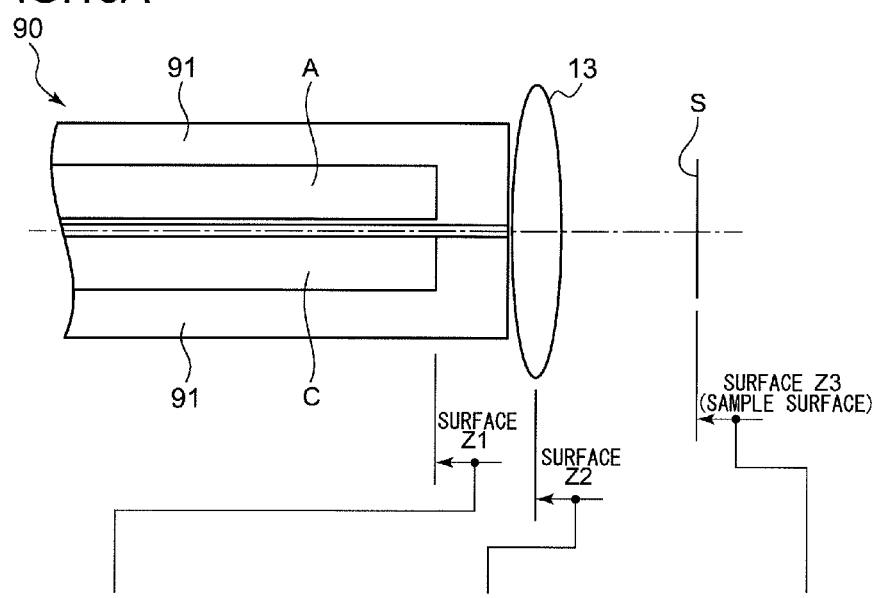
FIGS. 10A-10D illustrate a fluorescence light detection device according to yet another embodiment of the present invention.
Figure 10B:
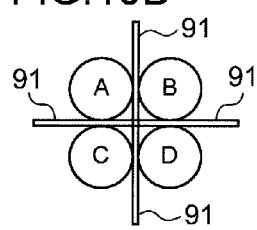
Figure 10C:
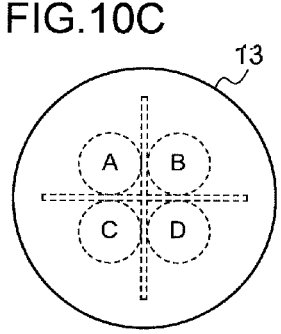
Figure 10D:
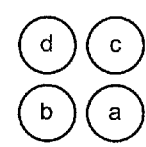

FIGS. 10A-10D illustrate a fluorescence light detection device 90 according to yet another embodiment of the present invention. FIG. 10A is a schematic overview of the fluorescence light detection device 90. FIGS. 10B-10D are cross-sectional views of the fluorescence light detection device 90 at surfaces Z1-Z3 (Z3 represents a surface in or on the sample) perpendicular to the plane of paper. These cross-sectional views show relative positions of a plurality of fibers and a plurality of reflective plates mounted in the device, and the positions of spots produced by the respective fibers via the objective lens 13. It is assumed that the objective lens 13 is an optical system that forms an inverted image. FIG. 10D is a schematic view of the positions of spots formed on a surface in or on the sample.

The fluorescence light detection device 90 according to the embodiment is provided with four fibers A-D and four reflective plates 91. Each of the reflective plates 91 is formed with a reflective surface on both surfaces. The four fibers A-D are arranged such that the optical axes are parallel to each other. The fibers A-D are arranged in a square shape when the fiber end surface is seen from the direction of optical axis of the fiber. Each of the four reflective plates 91 is positioned between adjacent fibers when the fiber end surface is seen from the direction of optical axis of the fiber. The angle formed by two adjacent reflective plates 91 is 90°.

In this embodiment, given that the fiber A is an excitation light fiber, and the fibers B, C, and D are fluorescence light fibers for collecting fluorescence light of different wavelengths, rays of excitation light emitted from the fiber A that travel without being reflected by any of the reflective plates is focused by the objective lens 13 to form an image on a spot a shown in FIG. 10D. Rays that travel by being reflected only once by one of the reflective plates is focused also by the objective lens 13 to form an image on a spot b or c. Rays that travel by being reflected twice by one of the reflective plates is focused also by the objective lens 13 to form an image on a spot d. Due to the action of the reflective plates 91, the fibers B, C, and D are capable of collecting fluorescence light produced at the spots a, b, c, and d using the objective lens 13. Therefore, the intensity of fluorescence light detected is higher than in the case where the four reflective plates 91 are not provided. In further accordance with the fluorescence light detection device 90 of this embodiment, fluorescence light of three wavelengths can be measured at the same time. It is assumed here that the objective lens 13 comprising an optical system that forms an inverted image is used. The relative positions of the spots that result when the objective lens 13 comprising an optical system that forms an erect image is used will be known by interpreting the spot positions in FIG. 10D such that d→a, c→b, b→c, and a→d.

In further accordance with the fluorescence light detection device 90 according to this embodiment, it is possible to emit excitation light of two different wavelengths from two of the fibers A-D and to measure fluorescence light of two arbitrary wavelengths, or to emit excitation light of three different wavelengths and to measure fluorescence light of one arbitrary wavelength, etc.

Figure 11A:
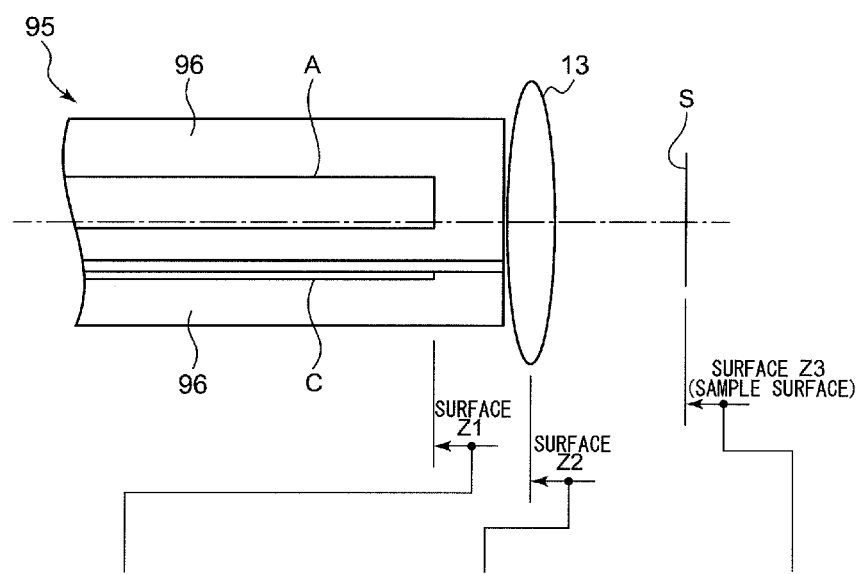
FIGS. 11A-11E illustrate a fluorescence light detection device according to yet another embodiment of the present invention.
Figure 11B:
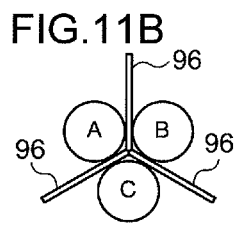
Figure 11C:
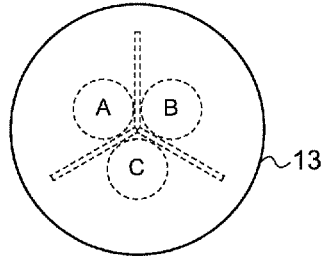
Figure 11D:
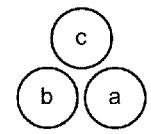

FIGS. 11A-11E illustrate a fluorescence light detection device 95 according to yet another embodiment of the present invention. FIG. 11A is a schematic overview of the fluorescence light detection device 95. FIGS. 11B-11D are cross-sectional views of the fluorescence light detection device 95 at surfaces Z1-Z3 (Z3 represents a surface in or on the sample) perpendicular to the plane of paper. These cross-sectional views show relative positions of a plurality of fibers and a plurality of reflective plates mounted in the device, and the positions of spots produced by the respective fibers via the objective lens 13. It is assumed that the objective lens 13 is an optical system that forms an inverted image. FIG. 11D is a schematic view of the positions of spots formed on a surface in or on the sample.

The fluorescence light detection device 95 according to this embodiment is provided with three fibers A-C and three reflective plates 96. Each of the reflective plates 96 is formed with a reflective surface on both surfaces. The three fibers A-C are arranged such that the optical axes are parallel to each other. The fibers A-C are arranged in a triangular shape when the fiber end surface is seen from the direction of optical axis of the fiber. Each of the three reflective plates 96 is positioned between adjacent fibers when the fiber end surface is seen from the direction of optical axis of the fiber. The angle formed by two adjacent reflective plates 96 is 120°.

Figure 11E:
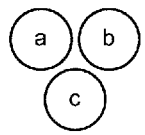

In this embodiment, given that the fiber A is an excitation light fiber, and the fibers B and C are fluorescence light fibers for collecting fluorescence light of different wavelengths, rays of excitation light emitted from the fiber A that travel without being reflected by any of the reflective plates is focused by the objective lens 13 to form an image on a spot a shown in FIG. 11D. Rays that travel by being reflected only once by one of the reflective plates is focused also by the objective lens 13 to form an image on a spot b or c. Due to the action of the reflective plates 96, the fibers B and C are capable of collecting fluorescence light produced at the spots a, b, and c using the objective lens 13. Therefore, the intensity of fluorescence light detected is higher than in the case where the three reflective plates 96 are not provided. In further accordance with the fluorescence light detection device 95 of this embodiment, fluorescence light of two wavelengths can be measured at the same time. It is assumed here that the objective lens 13 comprising an optical system that forms an inverted image is used. The positions of the spots that result when the objective lens 13 comprising an optical system that forms an erect image will be as shown in FIG. 11E.

It is assumed that four fibers are used in the embodiment shown in FIGS. 10A-10D and three fibers are used in the embodiment shown in FIGS. 11A-11E. Alternatively, the number of fibers may be increased to 5, 6, 7, . . . . Given that the number of fibers is n, a total of 2n reflective surfaces will be necessary. In case a reflective plate formed with a reflective surface on both surfaces is used as a reflective member, a total of n reflective plates will be necessary. In this case, each of the n fibers is arranged at a vertex of a polygon with n sides when the fiber end surface is seen from the direction of optical axis of the fiber. The reflective plates are arranged such that two reflective surfaces are positioned between adjacent fibers when the fiber end surface is seen from the direction of optical axis of the fiber.

Described above is an explanation based on an exemplary embodiment. The embodiment is intended to be illustrative only and it will be obvious to those skilled in the art that various modifications to constituting elements and processes could be developed and that such modifications are also within the scope of the present invention.

What is claimed is:

1. A fluorescence light detection device configured to irradiate a test object with excitation light and detect fluorescence light produced from the test object due to the excitation light, comprising:
    an excitation light fiber having an excitation light emitting end configured to emit excitation light;
    a fluorescence light fiber having a fluorescence light incident end on which fluorescence light is incident;
    an objective lens arranged between where the excitation light emitting end and the fluorescence light incident end are located, and the test object; and
    a reflective member arranged between where the excitation light emitting end and the fluorescence light incident end are located, and the objective lens, and having two reflective surfaces facing in opposite directions, wherein
    the two reflective surfaces of the reflective member are positioned between an optical axis of the excitation light fiber and an optical axis of the fluorescence light fiber.

2. The fluorescence light detection device according to claim 1, wherein
    the two reflective surfaces of the reflective member are parallel to an optical axis of the excitation light fiber and an optical axis of the fluorescence light fiber.

3. The fluorescence light detection device according to claim 1, wherein
    the center between the two reflective surfaces is located at the center between an optical axis of the excitation light fiber and an optical axis of the fluorescence light fiber.

4. The fluorescence light detection device according to claim 1, wherein
    the reflective member is placed so that the two reflective surfaces extend from the excitation light emitting end and the fluorescence light incident end to a position in front of the objective lens.

5. The fluorescence light detection device according to claim 4, wherein
    the reflective member extends beyond the excitation light emitting end and the fluorescence light incident end and into a space between the excitation light fiber and the fluorescence light fiber.

6. The fluorescence light detection device according to claim 1, wherein
    the reflective member is a reflective plate configured to reflect light on both front and back surfaces.

7. The fluorescence light detection device according to claim 1, wherein
    the reflective member is provided with two cuboid prisms placed such that flat surfaces thereof are spaced apart at a predetermined distance.

8. The fluorescence light detection device according to claim 1, further comprising:
    an objective reflective member placed between the objective lens and the test object and having two reflective surfaces facing mutually opposite directions.

9. The fluorescence light detection device according to claim 1, wherein
    the objective lens is configured as a single lens or a combination of a plurality of lenses.

10. The fluorescence light detection device according to claim 1, wherein
    the objective lens is provided with two lenses and an inter-lens reflective member placed between the two lenses and having two reflective surfaces facing mutually opposite directions.

11. The fluorescence light detection device according to claim 1, further comprising:
    a fluorescence light selection filter in front of the fluorescence light incident end.

12. The fluorescence light detection device according to claim 1, further comprising:
    an excitation light selection filter in front of the excitation light emitting end.

13. A fluorescence light detection device configured to irradiate a test object with excitation light and detect fluorescence light produced from the test object due to the excitation light, comprising:
    one or a plurality of excitation light fibers having an excitation light emitting end;
        one or a plurality of fluorescence light fibers having a fluorescence light incident end on which fluorescence light is incident;
        an objective lens arranged between where the excitation light emitting end and the fluorescence light incident end are located, and the test object; and
        a reflective member arranged between where the excitation light emitting end and the fluorescence light incident end are located, and the objective lens, and having a total of 2n reflective surfaces, given that the total number of excitation light fibers and fluorescence light fibers is n, wherein
        the excitation light fiber and the fluorescence light fiber are arranged such that optical axes are parallel to each other,
        each of the excitation light fibers and the fluorescence light fibers is arranged at a vertex of a polygon with n sides when the fiber end surface is seen from the direction of optical axis of the fiber, and
        the reflective plates are arranged such that the two reflective surfaces are positioned between adjacent fibers when the fiber end surface is seen from the direction of optical axis of the fiber.

14. A method of detecting fluorescence light from a test object by using the fluorescence light detection device according to claim 1.

15. The method of detecting fluorescence light according to claim 14, comprising:
    adjusting a working distance of the objective lens such that a signal obtained based on the fluorescence light is maximized and/or variation in signals obtained based on the fluorescence light is minimized.

16. The method of detecting fluorescence light according to claim 14, comprising:
    adjusting the angle formed by the optical axis of the excitation light fiber and/or the fluorescence light fiber and a surface of the test object such that a signal obtained based on the fluorescence light is maximized and/or variation in signals obtained based on the fluorescence light is minimized.

* * * * *